(12) United States Patent
Tarnawski

(10) Patent No.: US 11,562,514 B2
(45) Date of Patent: Jan. 24, 2023

(54) INSTRUMENT ANALYZERS, DATA DISPLAYS, AND DISPLAY METHODS

(71) Applicant: Siemens Healthcare Diagnostics Inc., Tarrytown, NY (US)

(72) Inventor: Dariusz Tarnawski, Hackettstown, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/250,213

(22) PCT Filed: Aug. 28, 2019

(86) PCT No.: PCT/US2019/048443
§ 371 (c)(1),
(2) Date: Dec. 16, 2020

(87) PCT Pub. No.: WO2020/051028
PCT Pub. Date: Mar. 12, 2020

(65) Prior Publication Data
US 2021/0264650 A1    Aug. 26, 2021

Related U.S. Application Data

(60) Provisional application No. 62/728,264, filed on Sep. 7, 2018.

(51) Int. Cl.
*G06T 11/20* (2006.01)
*G16H 40/20* (2018.01)
(Continued)

(52) U.S. Cl.
CPC ........ *G06T 11/206* (2013.01); *G06F 16/9024* (2019.01); *G06T 11/001* (2013.01);
(Continued)

(58) Field of Classification Search
CPC ..... G06T 11/206; G06T 11/001; G16H 40/20; G16H 10/40; G16H 15/00; G16H 40/63; G06F 16/9024
See application file for complete search history.

(56) References Cited

U.S. PATENT DOCUMENTS 5,461,708 A    10/1995    Kahn
5,581,678 A    12/1996    Kahn
(Continued)

FOREIGN PATENT DOCUMENTS

CN    105929800    9/2016
WO    2013016038    1/2013

OTHER PUBLICATIONS

International Search Report for PCT/US2019/048443 dated Nov. 19, 2019.
(Continued)

*Primary Examiner* — Maurice L. McDowell, Jr.

(57) ABSTRACT

A data display includes a grid including: a first column configured to display particular data values of a first data parameter; a plurality of rows, each row configured to display a particular data value of the first data parameter in the first column; and a second column including a vertically-extending graph, wherein the particular data value in one or more of the plurality of rows is plotted as a data point horizontally aligned with a corresponding row on the vertically-extending graph, wherein a plurality of data points display moving data values of the first data parameter. Other devices such as instrument analyzers and methods of displaying data are disclosed.

18 Claims, 6 Drawing Sheets

(51) Int. Cl.
*G16H 10/40* (2018.01)
*G06F 16/901* (2019.01)
*G06T 11/00* (2006.01)
*G16H 15/00* (2018.01)
*G16H 40/63* (2018.01)

(52) U.S. Cl.
CPC .............. *G16H 10/40* (2018.01); *G16H 40/20* (2018.01); *G16H 15/00* (2018.01); *G16H 40/63* (2018.01)

(56) References Cited

U.S. PATENT DOCUMENTS

| | | | |
|---|---|---|---|
| 6,269,276 B1 | 7/2001 | Akhavan et al. | |
| 6,384,847 B1* | 5/2002 | Rabenhorst | G06T 11/206 715/764 |
| 7,680,605 B2 | 3/2010 | Yung et al. | |
| 7,711,503 B2 | 5/2010 | Yundt-Pacheco | |
| 8,838,462 B2 | 9/2014 | Juncker et al. | |
| 9,262,310 B2 | 2/2016 | Karch et al. | |
| 9,507,809 B2 | 11/2016 | Burdette et al. | |
| 9,665,956 B2 | 5/2017 | Shikhman | |
| 10,783,191 B1* | 9/2020 | Caudy | G06T 11/206 |
| 2005/0179684 A1* | 8/2005 | Wallace | G06T 11/206 345/419 |
| 2006/0155487 A1 | 7/2006 | Yundt-Pacheco | |
| 2008/0148140 A1 | 6/2008 | Nakano | |
| 2008/0183639 A1* | 7/2008 | DiSalvo | G06Q 40/06 705/36 R |
| 2008/0278495 A1* | 11/2008 | Minamide | G06T 11/206 345/440 |
| 2009/0160861 A1 | 6/2009 | Nakano | |
| 2012/0035945 A1 | 2/2012 | Jain et al. | |
| 2012/0245980 A1 | 9/2012 | Cook et al. | |
| 2013/0024130 A1* | 1/2013 | Zahniser | G01N 15/14 702/21 |
| 2013/0060603 A1 | 3/2013 | Wagner | |
| 2014/0028683 A1* | 1/2014 | Luo | G06T 11/206 345/440.2 |
| 2014/0316732 A1 | 10/2014 | Dupoteau | |
| 2015/0015504 A1* | 1/2015 | Lee | G06T 11/206 345/173 |
| 2015/0228097 A1* | 8/2015 | Matange | G06T 11/206 345/440 |
| 2015/0262396 A1* | 9/2015 | Devarajan | G06F 3/0486 345/440.1 |
| 2015/0278371 A1* | 10/2015 | Anand | G06F 16/338 707/723 |
| 2016/0026959 A1 | 1/2016 | Leber | |
| 2016/0275661 A1* | 9/2016 | Goard | G06T 11/206 |
| 2017/0004521 A1 | 1/2017 | Wagner et al. | |
| 2017/0032091 A1 | 2/2017 | Rudorfer et al. | |
| 2017/0092008 A1* | 3/2017 | Djorgovski | G06T 15/205 |
| 2017/0132815 A1* | 5/2017 | Peev | G06T 19/00 |
| 2017/0177201 A1* | 6/2017 | Disdero | G06F 16/248 |
| 2017/0185668 A1* | 6/2017 | Convertino | G06T 11/206 |
| 2017/0275674 A1 | 9/2017 | Norman et al. | |
| 2017/0285624 A1 | 10/2017 | Lesher | |
| 2018/0024901 A1* | 1/2018 | Tankersley | G06F 16/2379 707/694 |
| 2018/0032954 A1 | 2/2018 | Barnes et al. | |
| 2018/0239644 A1* | 8/2018 | Uesaka | G06F 9/5077 |
| 2018/0309061 A1* | 10/2018 | Chun | G06T 7/0004 |
| 2019/0220157 A1* | 7/2019 | Crouch | G06F 3/0484 |
| 2019/0370158 A1* | 12/2019 | Rivoir | G06F 11/3672 |
| 2020/0049675 A1* | 2/2020 | Ramirez | G01N 15/1012 |

OTHER PUBLICATIONS

"Orchard Software Laboratory Information System (LIS)", Allscripts Healthcare, LLC, (2015).

Karkalousos, Petros et al: "Chapter 17: Quality control in clinical laboratories"; Applications and Experiences in Quality Control, Intech, GB; pp. 331-360, Apr. 26, 2011.

Pearson, Derek et al: "Laboratory and Instrument Quality Control"; In: Clinical Trials in Osteoporosis Second Edition; Jan. 1, 2007, pp. 141-159.

Ayling, Pete et al: "A practical tool for monitoring the preformance of measuring systems in a laboratory network: report of an ACB Working Group"; Annals of Clinical Biochemistry: International Journal of Labaratory Medicine; vol. 54, No. 6, Mar. 16, 2017, pp. 702-706.

Glencross, Deborah K. et al: "Large-scale affordable Panleucogated CD4 testing with proactive internal and external quality assessment: In support of the South Africam national comprehensive care, treatment and menagment programme for HIV and ADIS"; Cytometry Part B: Clinical Cytometry; vol. 74B, No. S1, Jan. 1, 2008 (Jan. 1, 2008), pp. 40-51.

* cited by examiner

| TEST | INSTRUMENT | ASSESSED | STRING VALUE |
|---|---|---|---|
| ☐ AST | Instrument 1 | 1/6/2017 9:42:12 | 5.9 |
| ☐ AST | Instrument 1 | 1/7/2017 3:22:15 | 7.0 |
| ☒ AST | Instrument 1 | 1/7/2017 4:42:12 | 11.1 |
| ☐ AST | Instrument 1 | 1/7/2017 5:42:17 | 7.8 |
| ☐ AST | Instrument 1 | 1/7/2017 6:33:52 | 8.0 |
| ☐ AST | Instrument 1 | 1/7/2017 6:42:42 | 8.0 |
| ☐ AST | Instrument 1 | 1/8/2017 6:22:52 | 8.6 |
| ☐ AST | Instrument 1 | 1/8/2017 6:52:16 | 10.5 |
| ☐ AST | Instrument 1 | 1/8/2017 9:42:12 | 10.5 |
| ☐ AST | Instrument 1 | 1/8/2017 10:42:44 | 9.3 |
| ☐ AST | Instrument 1 | 1/8/2017 11:16:12 | 8.7 |
| ☐ AST | Instrument 1 | 1/9/2017 6:12:35 | 8.1 |
| ☐ AST | Instrument 1 | 1/9/2017 7:52:33 | 8.6 |
| ☐ AST | Instrument 1 | 1/9/2017 8:43:32 | 8.8 |

Figure 3B:
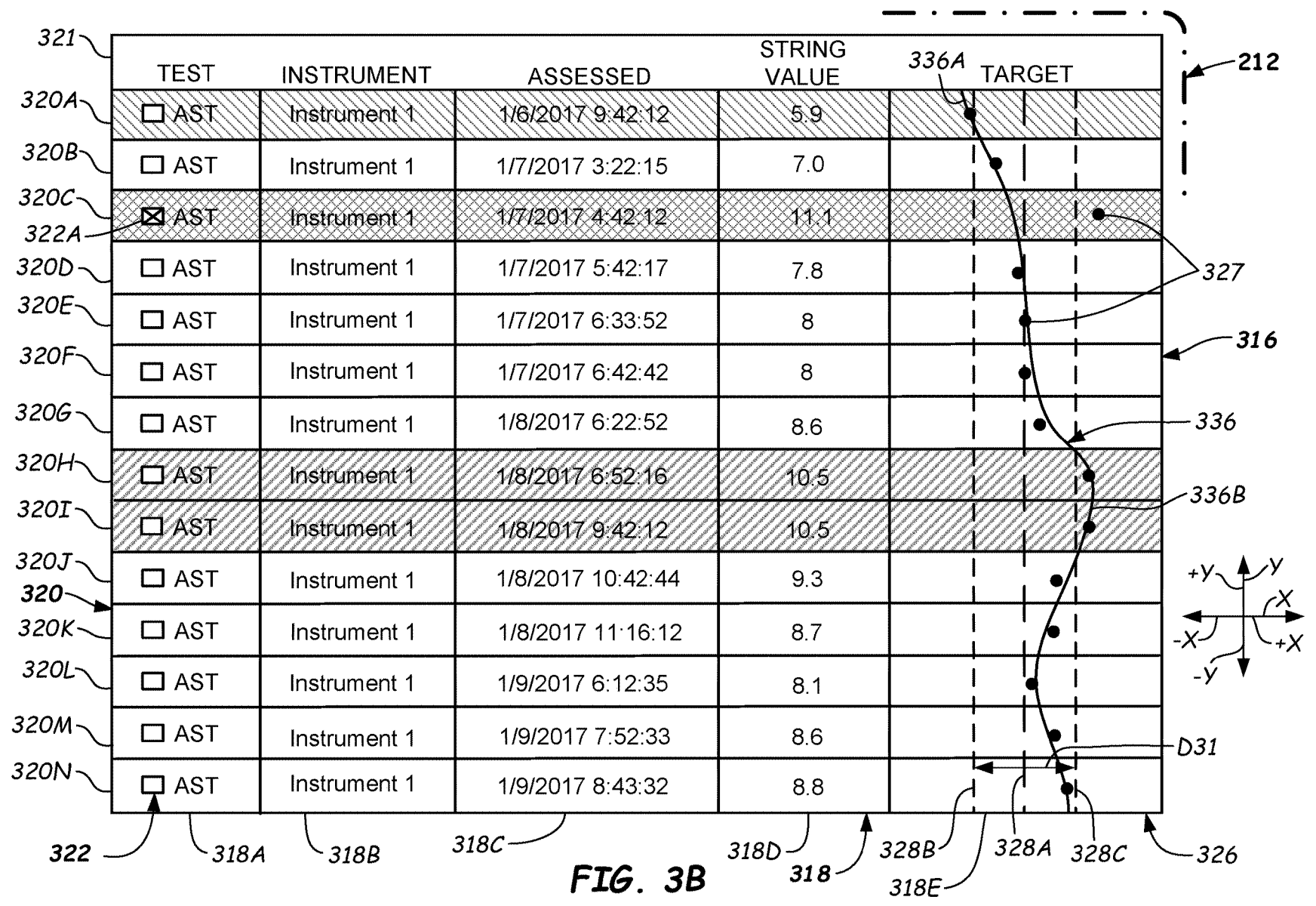

| TEST | INSTRUMENT | ASSESSED | STRING VALUE |
|---|---|---|---|
| ☐ AST | Instrument 1 | 1/6/2017 9:42:12 | 5.9 |
| ☐ AST | Instrument 1 | 1/7/2017 3:22:15 | 7.0 |
| ☒ AST | Instrument 1 | 1/7/2017 4:42:12 | 11.1 |
| ☐ AST | Instrument 1 | 1/7/2017 5:42:17 | 7.8 |
| ☐ AST | Instrument 1 | 1/7/2017 6:33:52 | 8 |
| ☐ AST | Instrument 1 | 1/7/2017 6:42:42 | 8 |
| ☐ AST | Instrument 1 | 1/8/2017 6:22:52 | 8.6 |
| ☐ AST | Instrument 1 | 1/8/2017 6:52:16 | 10.5 |
| ☐ AST | Instrument 1 | 1/8/2017 9:42:12 | 10.5 |
| ☐ AST | Instrument 1 | 1/8/2017 10:42:44 | 9.3 |
| ☐ AST | Instrument 1 | 1/9/2017 11:16:12 | 8.7 |
| ☐ AST | Instrument 1 | 1/9/2017 6:12:35 | 8.1 |
| ☐ AST | Instrument 1 | 1/9/2017 7:52:33 | 8.6 |
| ☐ AST | Instrument 1 | 1/9/2017 8:43:32 | 8.8 |

INSTRUMENT ANALYZERS, DATA DISPLAYS, AND DISPLAY METHODS

RELATED APPLICATIONS

This application claims priority to U.S. Provisional Application Ser. No. 62/728,264 entitled "VERTICAL PATIENT MOVING AVERAGE GRAPH ON RESULT GRID" filed on Sep. 7, 2018, the disclosure of which is hereby incorporated by reference in its entirety herein.

FIELD

The present disclosure relates to equipment analyzers, data displays, and methods of displaying data.

BACKGROUND

Patient specimen testing laboratories (referred to herein as "laboratories") may include a plurality of instruments configured to test and/or analyze specimens from patients. Test results generated by the instruments may drift over time and may yield inaccurate test results if not corrected. Some instruments may include processors or the like that perform quality control tests and measure quality control parameters of the instruments. These measured quality control parameters provide an indication of certain parameters of the instruments, which may indicate a relative accuracy of tests that are to be performed by the instruments.

Some laboratory products and/or instruments include displays that enable users to view such quality control parameters.

SUMMARY

According to a first aspect, a data display is provided. The data display comprises a grid including a first column configured to display data values of a first data parameter, a plurality of rows, each row configured to display a particular data value of the first data parameter in the first column, and a second column including a vertically-extending graph, wherein the particular data value in one or more of the plurality of rows is plotted as a data point horizontally aligned with a corresponding row on the vertically-extending graph, wherein a plurality of data points display moving data values of the first data parameter.

According to a second aspect, a method of displaying data is provided. The method includes displaying a first column, wherein the first column is configured to display particular data values of a first data parameter; displaying a plurality of rows, each row configured to display a particular data value of the first data parameter in the first column; and displaying a second column including a vertically-extending graph, wherein the particular data value in one or more of the plurality of rows is plotted as a data point horizontally aligned with a corresponding row on the vertically-extending graph, wherein a plurality of data points display moving data values of the first data parameter.

According to a third aspect, an instrument analyzer is provided. The instrument analyzer includes a data display comprising: a grid including: a first column configured to display data values of a first data parameter received from an instrument, a plurality of rows, each row configured to display a particular data value of the first data parameter in the first column, and a second column including a vertically-extending graph, wherein the particular data value in a row is plotted as a data point horizontally aligned with a corresponding row on the vertically-extending graph, wherein a plurality of data points display moving data values of the first data parameter received from the instrument.

BRIEF DESCRIPTION OF THE DRAWINGS

FIG. 3A illustrates a grid displayed on a data display of an instrument analyzer according to one or more embodiments.

FIG. 3B illustrates the data display of FIG. 3A with a best-fit line extending vertically in a vertically-extending graph according to one or more embodiments.

DETAILED DESCRIPTION

Figure 1:
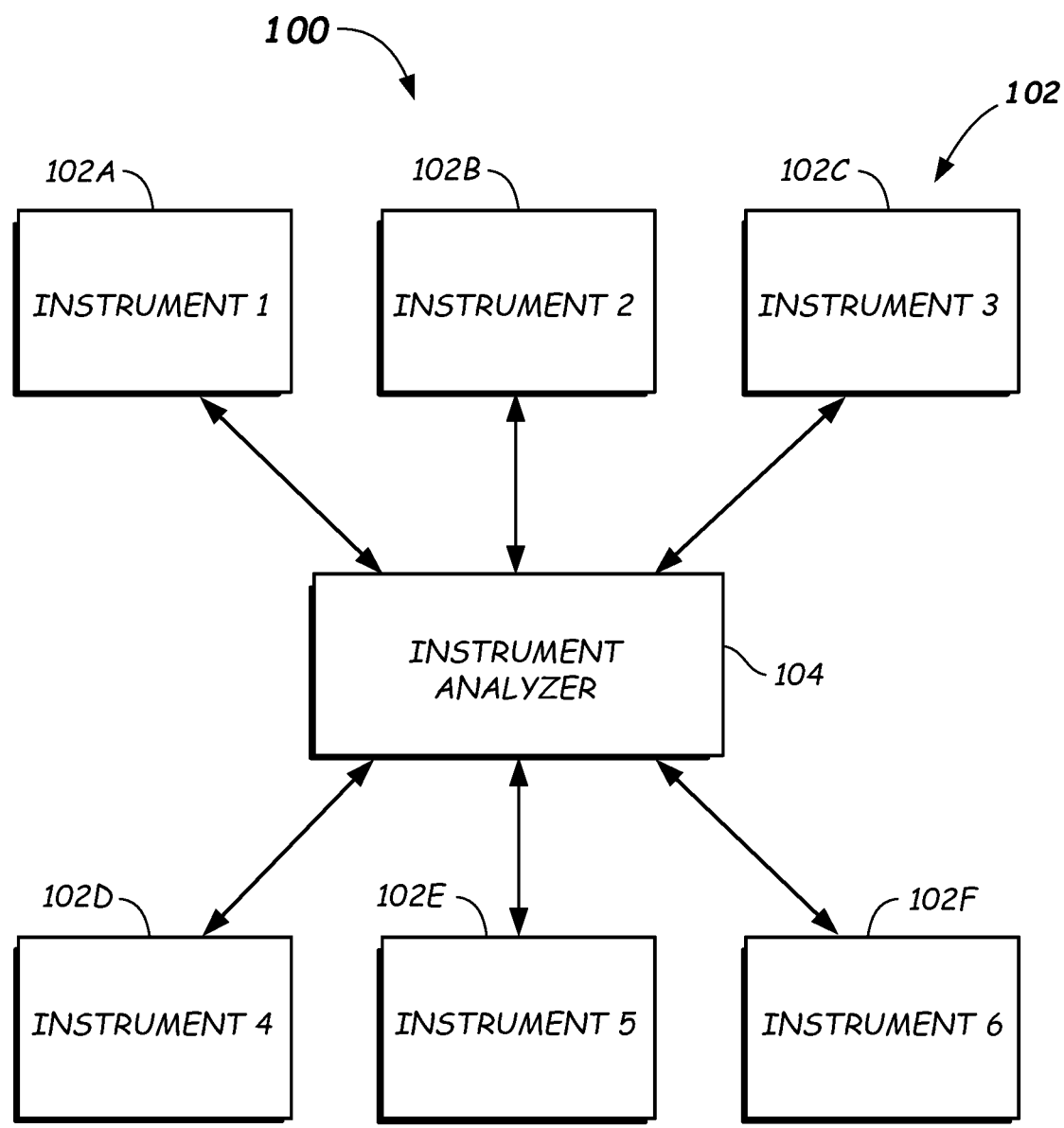
FIG. 1 illustrates a block diagram of a laboratory testing system including a plurality of instruments according to one or more embodiments.

Patient testing laboratories (referred to herein as "laboratories") may include a plurality of instruments adapted to test and analyze specimens (sometimes referred to as "samples") from patients. These instruments may test blood, urine, cerebrospinal fluid, or other samples taken from patients. In order to ensure precise and accurate test results, the instruments are maintained and also periodically calibrated so as to provide optimal performance. Calibration and maintenance cannot be performed too often because these procedures cause the instruments to be inoperable during calibration and maintenance. Moreover the calibrator samples also have an associated cost. However, if calibration and maintenance procedures are not preformed often enough, the precision of the tests performed by the instruments may decline or drift.

In some products and/or instruments, such as in vitro diagnostics (IVD) instruments, quality control data or patient moving average (PMA) data may be displayed in the form of a list displayed in a grid. The grid has columns that indicate certain quality control parameters. Such quality control parameters can be based on averages or standard deviation, for example. However, in conventional instruments there are no means to display quality control parameters based on the actual measured values in order to display patient moving average (PMA) results without multiple screens. In conventional products and/or instruments, users can navigate between multiple screens on a computer display in order to review graphs (in horizontal format) of the PMA or quality control results. For example, users may have to print the graphs and compare the printed graphs to one another in order to fully understand the data.

Sometimes the decline in precision of an instrument is very subtle and may not be obvious to a user. The subtle decline in precision may also not register as an issue with internal quality diagnostics of an instrument, such as quality control parameters, until the precision has declined a significant amount. One method of measuring changes or declines in instrument precision is by measuring or observing a PMA. PMA provides a moving average of values of patients test results measured by an instrument over time. A moving or drifting PMA over time may be indicative of an issue with the instrument and the issue may be detected before other internal tests indicate faults with the instrument. As a result of early detection, some results of tests performed by the instrument may not have to be discarded.

As an example, an instrument may measure a certain parameter in blood plasma or serum. Specimens from a significant number of the general population may have a measured value of 10.0, as an example, when measured using an ideal instrument, which is calibrated and operating optimally. The value of 10.0 may then be used as the target PMA. Specimens tested over time may have values greater than and less than 10.0, but the average, under ideal circumstances should be 10.0. If, over time, the PMA value drifts, such as to 10.2, embodiments of the disclosure allow the operator of the instrument to detect a possible issue with precision and take action to fix and/or calibrate the instrument. The PMA may be used to detect drift along with other tests by the instruments, such as quality control tests.

Data displays, methods of displaying data, instruments, instrument analyzers, and processors described herein overcome the above-described issues. The data displays, methods of displaying data, instruments, instrument analyzers, and/or processors may include or be part of a graphical user interface (GUI) to enable a user to quickly analyze data produced by the instruments. In some embodiments, the data display may enable users to display PMA or quality control results in a unique grid format within an associated vertically-extending graph.

The vertically-extending graph may include measured and/or calculated data values that are plotted on a horizontal axis (e.g., an x-axis) and variables, such as time, that are plotted on a vertical axis (e.g., a y-axis). The grid may display data values measured by instruments in rows that correspond to data points plotted on the vertically-extending graph. The vertically-extending graph may, upon input from a user, display trend lines that enable the user to quickly assess functionality (e.g., precision and/or calibration) of the instruments and predict future functionality or trends.

In some embodiments, one or more data values that are outside of predetermined values may be flagged or otherwise highlighted on the vertically-extending graph or in the corresponding rows in the grid to provide an indicator of possible testing anomalies. Flagging may include displaying different shapes of data points and/or different colors of data points and/or rows or any other suitable indicator. For example, one or more data points within the predetermined range of values may be displayed using a first style and one or more data points outside the predetermined range may be displayed using a second style. Flagging may also include providing a first intensity of displayed information for one or more data points within the predetermined range of values and a second intensity for one or more data values outside the predetermined range of values. Parameters displayed in the grid may include test measurements and/or test results, instrument names, date and time of the tests performed, test parameter names, and other information and data values that enable users to evaluate the function of the instrument(s).

The vertically-extending graph may include indicia indicating the predetermined data values and/or fixed data values. For example and with regard to the previous example, the vertically-extending graph may include vertically-extending lines on each side of the predetermined data value. The vertically-extending lines may indicate a range of acceptable data values of a particular parameter. The predetermined data value may be a nominal test value. The above-described flagging may occur when a data values is outside of the acceptable data values. In some embodiments, the flagging may occur when data values are consistently outside the acceptable data values for a predetermined period of time or a predetermined number of data samples.

The apparatus and methods described herein provide data from the instrument(s) in a format that can be easily and quickly understood by users. For example, users do not have to access multiple programs, print multiple graphs, or access multiple pages to understand quality control data and/or PMA of the instruments. Thus, the productivity of the instruments and laboratories where the instruments operate is greatly improved. In addition, the data values plotted on the vertically-extending graph may be oriented horizontally, which enables users to easily read the data.

These and other embodiments of the apparatus, systems, and methods are described below with reference to FIGS. 1-5.

Reference is now made to FIG. 1, which illustrates a block diagram of a laboratory testing system 100. The laboratory testing system 100 may include a plurality of instruments 102 that are electrically coupled to an instrument analyzer 104 and in digital communication therewith. The embodiment of the laboratory testing system 100 depicted in FIG. 1 includes six instruments, which are referred to individually as instruments 102A-102F. Other embodiments of the laboratory testing system 100 may include fewer or more than six instruments. The laboratory testing system 100 may be a part of or coupled to a laboratory information system (e.g., LIS 216—FIG. 2) or a data management system (not shown). For example, the instrument analyzer 104 or portions of the instrument analyzer 104 may be incorporated into middleware in a laboratory information system or other data management system. The instruments 102 may include devices that analyze chemistry, immune-assays (IA), urinalysis, hematology, and/or other chemicals of specimens. The instruments 102 may perform other types of analysis of specimens.

The instruments 102 may require calibration and maintenance in order to provide accurate test results over time. For example, one or more of the instruments 102 may perform testing by measuring light absorbed by or emitted by a patient sample. Thus, one or more of the instruments 102 may include light transmitters and/or light receivers with light paths extending to or through a sample test location. Should the light paths, the light transmitter, and/or the light receiver become contaminated, the test results provided by the instrument may become erroneous. Some of the instruments 102 may heat samples prior to and/or during testing. Should heating elements in these instruments deteriorate, the resulting tests may become erroneous. These testing anomalies of the instruments 102 may occur slowly over time and may not be quickly detected by internal testing, such as quality control testing or the like.

The instruments 102 and/or the instrument analyzer 104 in accordance with aspects of the disclosure may calculate and/or display patient moving averages (PMAs), which indicate the drift of an instrument over time. PMA is a measure of the trend in test results over time. For example, if the PMA tends to rise over time, the rise may be indicative that the instrument is in need of calibration or repair. If the PMA has a quick rise and then returns to an ideal value shortly thereafter, the short-term rise may be indicative of an average of patient sample tests just happening to be high and may not indicate an issue with the instrument.

As an example, one of the instruments 102 may generate a value, such as 8.0 as an ideal value of patient samples. Some patient samples may yield lower results, such as 7.6, and some patient samples may yield higher results, such as 8.4. The PMA should, thus, be about 8.0, although it may drift for a while up to 8.2 or down to 7.8 depending on other patient samples being tested. However, the PMA should return within a predetermined range centered about 8.0. Should the PMA rise, such as to 8.4 for a long period of time, or fall, such as to 7.6 for a long period of time, the rise or fall may indicate that the instrument is in need of calibration and/or maintenance.

Figure 2:
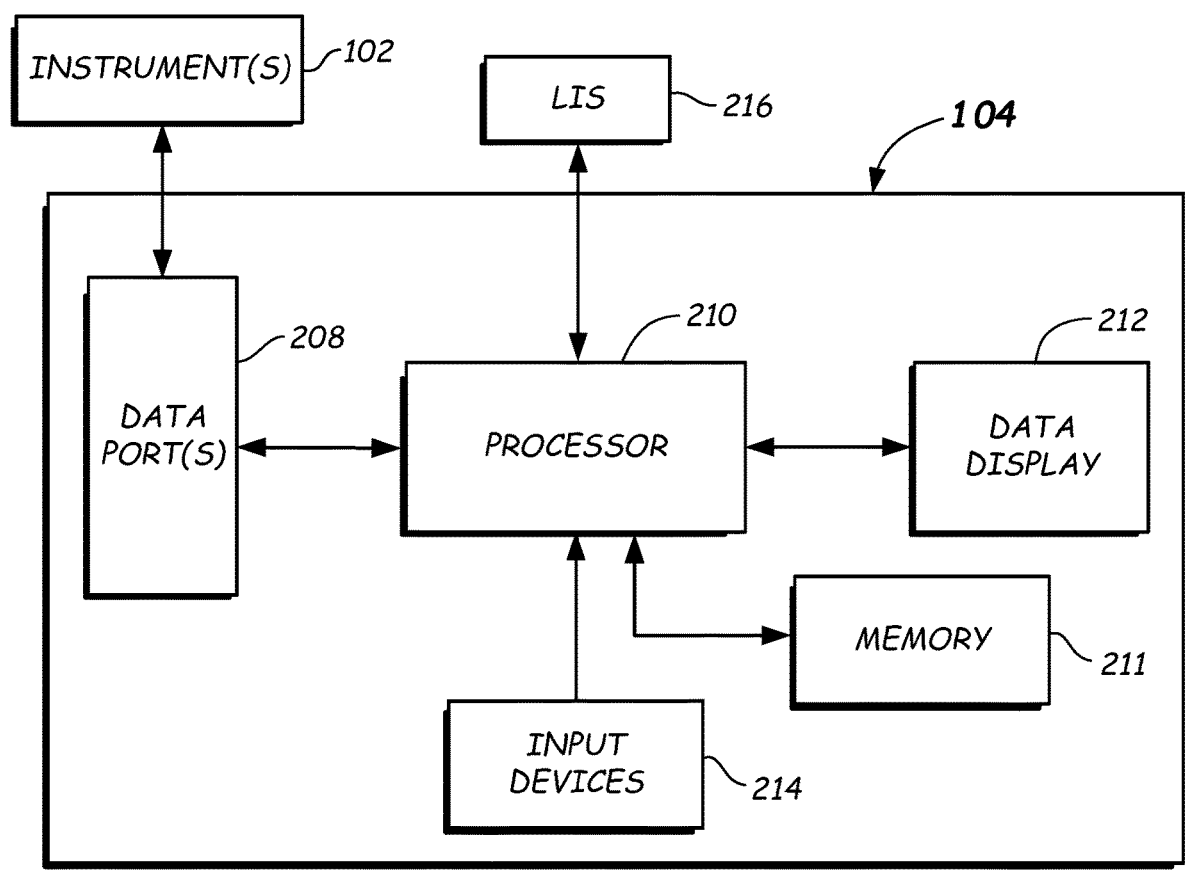
FIG. 2 illustrates a block diagram of an instrument analyzer used in a laboratory testing system according to one or more embodiments.

Additional reference is made to FIG. 2, which illustrates a block diagram of an example of the instrument analyzer 104. In some embodiments, some or all the components and/or methods of the instrument analyzer 104 may be located and/or performed by a data server. Optionally, some or all the components and/or methods of the instrument analyzer 104 may be carried out by an individual instrument 102. The instrument analyzer 104 may include one or more data ports 208 that are configured to couple to the instrument(s) 102. The one or more data ports 208 may be configured to receive data from the instrument(s) 102 and/or transmit instructions to the instrument(s) 102. In some embodiments, a single data port may couple to all the instruments 102. The one or more data ports 208 may be one or more wired data lines or one or more wireless communication devices that receive and transmit signals by radio frequencies (RF), or other wireless communication, for example. The data ports 208 may include other devices.

The data ports 208 may be coupled to a processor 210, which may be a suitable microprocessor configured to process data received from the instruments 102, carry out executable programs, and generate instructions to transmit to the instruments 102. The processor 210 may also be coupled to a data display 212 that may be part of a graphical user interface, wherein signals (e.g., digital signals) generated by the processor 210 cause the data display 212 to display certain images and data as are described herein. The data display may be a display screen (such as a LED, LCD or other display monitor), a display surface such as a projection surface, or other suitable display media. Input devices 214 may be coupled to the processor 210. The input devices 214 may include a computer mouse and keyboard that enable a user to input information and commands to the processor 210. The input devices 214 may include other devices. The processor 210 depicted in FIG. 2 may be coupled to a laboratory information system (LIS) 216, which is illustrated as being a separate device. Processor 210 may be coupled to a suitable memory 211 which may store data from the instruments 102 as well as programmed instructions and executable code.

In some embodiments, the processor 210 may transmit signals to the instruments 102 and may receive signals from the instruments 102 via the data ports 208. The signals may contain data and/or instructions. For example, the processor 210 may transmit instructions to the instruments 102 instructing one or more of the instruments 102 to transmit specific data or to run specific programs, such as calculating the PMA. The instruments 102 may transmit data, such as test results, quality control data, and/or PMA, to the processor 210. In some embodiments, the processor 210 may calculate values, such as PMA, based on test results. The test results may contain particular data values related to tests performed on patient specimens and/or on quality control specimens.

In some embodiments, the LIS 216 may instruct the processor 210 to retrieve data from the instruments 102. In some embodiments, the instrument analyzer 104 may be implemented into one or more of the instruments 102. Thus, the data display 212 may be a display on an instrument. In other embodiments, the instrument analyzer 104 may be at least partially incorporated into the LIS 216. Thus, the processing described herein may be executed with middleware or the like running in the LIS 216, such as on an LIS server or middleware server.

The processor 210 may format the data for display on the data display 212. Additional reference is made to FIG. 3A, which illustrates an embodiment of data, including particular data values, formatted for being displayed by the data display 212. Only a portion of the data display 212 is shown dotted, but that data display 212 can have any suitable shape, such as square or rectangular, that is of a suitable size for display of the data values, plots, and images. The data values, which may be PMA values or quality control values, may be displayed in a grid 316 on the data display 212, wherein the grid 316 may include lines, for example, forming one or more columns 318 (e.g., vertical columns) and one or more rows 320 (e.g., horizontal rows). The rows 320 are referred to individually as the first through the fourteenth rows 320A-320N, respectively. One or more of the columns 318 may be configured to display data values of a data parameter provided by one of the instruments 102 (FIG. 1) or calculated by the processor 210 (FIG. 2). One or more of the rows 320 may be configured to display a particular data value of a test parameter, such as a particular data value from a test that was completed by one of the instruments 102, such as a patient test or a quality control test. The grid 316 may include a header 321 that may include identifications (e.g., names) of various data parameters, wherein each data parameter may be aligned with one of the columns 318 and can comprise a heading thereof.

In the embodiment of the grid 316 depicted in FIG. 3A, a first column 318A is located under a "TEST" heading and may display data indicating a type of test that was performed. In some embodiments, the grid 316 displays information generated by a single instrument, so all the types of tests displayed in the first column 316A may be the same for a given instrument. In other embodiments, individual instruments may perform different tests, so the TEST heading may refer to different instruments.

The first column 318A may also display a plurality of check boxes 322, wherein individual boxes may be filled or empty and may provide information to the user of the instrument analyzer 104 as to whether the test corresponding to a particular row involved unusual circumstances. Thus, the check boxes 322 may provide users with a status of samples being tested. For example, if the sample being tested was from a patient with unusual conditions, the check box 322 related to that test may be filled. In the embodiment depicted in FIG. 3A, a check box 322A in the third row 320C is filled and indicates that the test involves unusual circumstances. As described in greater detail below, the filled check box 322A may indicate that the particular data values from the test may be out of a predetermined range of data values and may not be included into a PMA and/or other displayed information.

The embodiment of the grid 316 depicted in FIG. 3A may include a second column 318B that may be located under an "INSTRUMENT" heading in the header 321. The second column 318B may display information indicating the instrument that supplied particular data values for the rows 320 as described below. The instrument may be any of the plurality of instruments 102 (FIG. 1). In the embodiment depicted in FIG. 3A, only one instrument, instrument 1, which is the first instrument 102A (FIG. 2), is shown. In other embodiments, information, such as particular data values, from more than one instrument may be shown. For example, the grid 316 may include additional columns that display information and/or data for each of the other instruments (at least one additional column per instrument).

A third column 318C in the grid 316 may be located under an "ASSESSED" heading in the header 321 and may display information indicating when tests that generated particular data values in the rows 320 were performed. In the embodiment depicted in FIG. 3A, the third column 318C may display dates and times of the tests. In some embodiments, the dates and times may be displayed chronologically. The date may include day, month and year as well as hour, minute, and second.

A fourth column 318D may be located under a "STRING VALUE" heading in the header 321 and may display the particular data values for each of the tests performed. For example, if the instrument is performing a chemical analysis, the fourth column 318D may display the particular data values obtained from the chemical analysis of the specimens. In other embodiments, the particular data values displayed in the fourth column 318D can be quality control values calculated and/or measured by the instruments 102 undergoing quality control tests. For example, in the embodiment of FIG. 3A, the particular data values displayed in the fourth column 318D may be quality control values calculated and/or measured from the first instrument 102A. The fourth column 318D may also display other data values related to other data parameters as described below. In some embodiments, the particular data values displayed in the fourth column 318D may be calculated values, such as calculate by the processor 210 (FIG. 2).

The grid 316 may include or be adjacent a fifth column 318E that includes a vertically-extending graph 326. In some embodiments, the vertically-extending graph 326 may be located between columns 318 rather than being located at the edge of the grid 316 as shown in FIG. 3A. The vertically-extending graph 326 may include one or more data points 327 corresponding to one or more of the particular data values, wherein the horizontal placement (plotting) of a data point on the vertically-extending graph 326 is dependent on a particular data value. For example, high data values may be located in +x-positions relative to an x-axis of the vertically-extending graph 326 and low data values may be located in −x-positions. The data points 327 may be equally spaced relative to a y-axis and aligned with and within the respective rows 320. In some embodiments, the data points 327 are chronological, wherein data points 327 toward a +y-direction reflect particular data values of tests performed first and data points 327 toward a −y-direction reflect particular data values of recently-performed tests. In such embodiments, the vertically-extending graph 326 may display moving data values thus displaying how the data changes over time for a particular instrument and test.

The vertically-extending graph 326 may include one or more vertically-extending lines. In the embodiment depicted in FIG. 3A, the vertically-extending graph 326 may include a central axis or a first axis 328A, which represents ideal values for the particular data values in the fourth column 316D. In the embodiment depicted in FIG. 3A, the vertically-extending graph 326 may include a second axis 328B located on a first side (e.g., left side) of the first axis 328A. The vertically-extending graph 326 may also include a third axis 328C located on a second side (e.g., right side) of the first axis 328A. The second axis 328B may be spaced from the third axis 328C by a distance D31 and may be parallel to the third axis 328C. The distance D31 may represent a predetermined range of data values. The predetermined range of data values may be a range of target values for the particular data values displayed in the fourth column 318D. In some embodiments, the predetermined range of data values represents acceptable data values for the particular data values that are displayed in the fourth column 318D.

In the examples described below, the first axis 328A represents a fixed data value of 8.0, which may be an ideal data value for the particular data values displayed in the fourth column 318D. The second axis 328B may represent a fixed data value of 6.0, which may represent a lowest target data value or acceptable data value for the particular data values displayed in the fourth column 318D. The third axis 328C may represent a fixed data value of 10.0, which may represent a highest target data value for the particular data values displayed in the fourth column 318D. The predetermined range of data values may be 4.0, which is the range represented by the distance D31. The axes and the distance D31 may represent other fixed data values and ranges of data values.

Reference is made to the first row 320A, which displays information related to a first test result. A check box 322B in the first column 318A is not checked, indicating that the particular data value in the fourth column 318D was not obtained via unusual circumstances. Accordingly, the status of the sample tested may be normal. The second column 318B in the first row 320A indicates that the information and data displayed was obtained from the first instrument 102A (FIG. 1). The third column 318C displays a date and time when the particular data value displayed in the fourth column 318D was collected from the first instrument 102A. The fourth column 318D displays the particular data value obtained from the first instrument 102A. In the embodiment of FIG. 3A, the particular data value displayed in the fourth column 318D is 5.9, which is slightly below the lowest target value of 6.0 shown by the second axis 328B. The vertically-extending graph 326 includes a first data point 327A located slightly to the left of the second axis 328B, which corresponds to a value of 5.9 on the vertically-extending graph 326. The first data point 327A is in horizontal alignment with the first row 320A.

The second row 320B includes data from the first instrument 102A from test(s) performed at a time later than the data in the first row 320A. The data in the second row 320B includes a particular data value of 7.0 displayed in the fourth column 318D, which is plotted as a second data point 327B on the vertically-extending graph 326 between the second axis 328B and the first axis 328A. The value of 7.0 is within the predetermined range of data values depicted by the distance D31.

The third row 320C includes data from the first instrument 102A from test(s) performed at a later time than data displayed in the second row 320B. The data in the third row 320C include a particular data value of 11.1 (column 318D), which is plotted on the vertically-extending graph 326 as a third data point 327C to the right of the third axis 328C. The particular data value of 11.1 may be considered significantly beyond the upper range represented by the third axis 328C. In addition, the box 322A in the first column 318A is checked to indicate that the data value may be an anomaly or that the status of the sample is unusual. For example, the data value of 11.1 may have been obtained from a sample provided by a patient with unusual medical conditions. In some embodiments, the check box 322A being checked may indicate that the corresponding particular data value is not used in processing, such as determining the patient moving average or a best-fit line.

Additional reference is made to FIG. 3B, which illustrates the grid 316 of FIG. 3A with a best-fit line 336 extending vertically in the vertically-extending graph 326. A user may provide input via the input devices 214 (FIG. 2) that cause various data, such as the best-fit line 336, to be calculated and displayed on the grid 316. The best-fit line 336 may be calculated using the particular data values in the fourth column 318D. The best-fit line 336 may provide a user with information showing trends in the particular data values displayed in the fourth column 318D. Best-fit line 336 may be a graph of any suitable mathematical function or smoothing of the data. The best-fit line 336 depicted in FIG. 3B includes a first portion 336A that is less than the fixed data value of the second axis 328B and a second portion 336B that is greater than the fixed data value of the third axis 328C. The first portion 336A and the second portion 336B may provide the user with information regarding the status of the first instrument 102A (FIG. 1). For example, because the best-fit line 336 did not remain below the second axis 328B or above the third axis 328C for one or more extended periods of time, the user may assume that the first instrument 102A is operating correctly based solely on the best-fit line 336. If the best-fit line 336 remained either below the second axis 328B or above the third axis 328C for one or more long periods of time, the user may suspect that the first instrument 102A is in need of maintenance, such as re-calibration.

The grid 316 displayed in FIG. 3B provides indicators to a user that one or more of the particular data values displayed in the fourth column 318D is out of the range of the predetermined range of data values. The indicators may provide a first style, such as a first color, hatching, shading, and/or a first intensity, of the rows where the particular data values are beyond the predetermined range of data values. The remaining rows may be displayed in a second style, such as a second color, hatching, shading, or intensity. In some embodiments, the indicators may be applied to the data points 327 and/or some or all of the best-fit line 336.

In the embodiment of FIG. 3B, the particular data value in the first row 320A is below the fixed data value represented by the second axis 328B. In response to the low particular data value, the first row 320A may be displayed in a first color that is different from a color of the remaining rows. In the embodiment of FIG. 3B, the particular data value of the third row 320C may be based on unusual circumstances. In response to the unusual circumstances, the third row 320C may be displayed in a second color that is different than the remaining rows and the color of the first row 320A. In the embodiment of FIG. 3B, the particular data values of the eighth row 320H and the ninth row 320I are greater than the fixed data value represented by the third axis 328C. In response to the high particular data values, the eighth row 320H and the ninth row 320I may be displayed in a third color that is different that the second color, the first color, and the color of the remaining rows.

Figure 4:
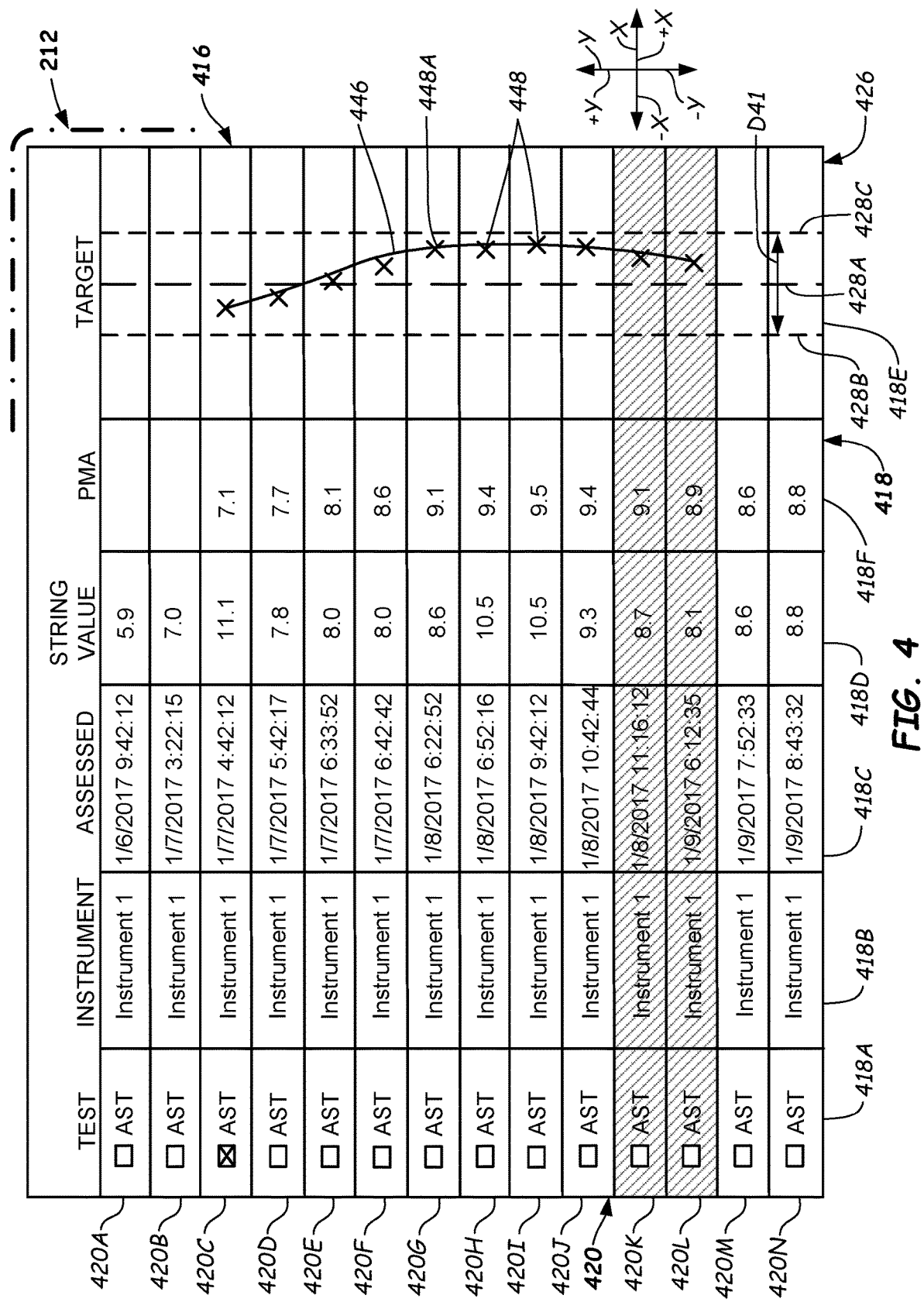
FIG. 4 illustrates the data display of FIG. 3A showing patient moving average (PMA) data values plotted on a line in a vertically-extending graph according to one or more embodiments.

Additional reference is made to FIG. 4, which illustrates a grid 416, which is similar to the grid 316, but with the addition of a sixth column 418F that displays and plots patient moving average (PMA) values. The grid 416 may include a plurality of columns 418, including a first column 418A that may be the same or similar to the first column 318A, a second column 418B that may be the same or similar to the second column 318B, a third column 418C that may be the same or similar to the third column 318C, and a fourth column 418D that may display the particular data values. A fifth column 418E may display a vertically-extending graph 426 that shows a moving average of the particular data values. The grid 416 may also include a plurality of rows 420 that are similar to the rows 320 (FIG. 3B) and are referred to individually as the first through fourteenth rows 420A-420N.

The grid 416 may display a patient moving average (PMA) 446 plotted in the vertically-extending graph 426. The PMA 446 may be calculated from the particular data values displayed in the fourth column 418D, wherein the particular data values may be measured data values from the first instrument 102A and/or quality control measurements from the first instrument 102A. The PMA 446 may be calculated based on other data. The PMA 446 may provide a running average of the particular data values displayed in the fourth column 418D. The PMA 446 may be plotted based on a plurality of moving average data points 448 that correspond to calculated patient moving average values displayed in the sixth column 418F.

The PMA values displayed in the sixth column 418F may be calculated based on a plurality of particular data values displayed in the fourth column 418D. As described below, the PMA may be an average of a plurality of particular data values. In some embodiments a moving average data point on the PMA 446 is plotted on the vertically-extending graph 426 in horizontal alignment with a particular row. The value of the moving average data point may be calculated based on the particular data value of the particular row in addition to particular data values in one or more rows above the particular row and/or one or more rows below the particular row. In some embodiments, the value of the moving average data point may be calculated from five particular data values, with one particular data value on the particular row in addition to two particular data values in two rows above the particular row and two particular data values in two rows below the particular row. In some embodiments, the value of the moving average data point may be calculated from seven particular data values, with one particular data value on the particular row in addition to three particular data values in three rows above the particular row and three particular data values in three rows below the particular row. In some embodiments, the value of the moving average data point may be calculated from seven or more particular data values, with one particular data value on the particular row in addition to three or more particular data values in three or more rows above the particular row and three or more particular data values in three or more rows below the particular row.

In the example of FIG. 4, the PMA data values may be calculated using a bin of five particular data values. The following example describes calculating a first PMA data value, which may be plotted on the vertically-extending graph 426 as a moving average data point 448A in horizontal alignment with the row 420G. In some embodiments, this first PMA data value is referred to as being on a first row for the purposes of describing calculations of the PMA. The first PMA data value may be calculated based on average of the particular data values in the row 420G, two rows (e.g., row 420E and row 420F) above the row 420G, and two rows (e.g., row 420H and row 420I) below the row 420G. In some embodiments, the rows above and below the row 420G may not be adjacent the row 420G or each other. The particular data value of the row 420G is 8.6 and the particular data values of the row 420E, the row 420F, the row 420H, and the row 420I are 8.0, 8.0, 10.5, and 10.5, respectively. Therefore, the first PMA value is 9.1. The process may be repeated for particular data values in the rows 420. In some embodiments, the bin of data values used to calculate the PMA may include seven or more particular data values. The PMA values may be displayed in the sixth column 418G.

The vertically-extending graph 426 may include a first axis 428A that may be a fixed value that represents an ideal or target PMA value. A second axis 428B may be a fixed value that represents a lowest target PMA value. A third axis 428C may be a fixed value that represents a highest target PMA value. A distance D41 between the first axis 428A and the second axis 428B may represent a predetermined range of values. A user may view the PMA 446 and determine whether the PMA 446 is tending away from the first axis 428A. Should the PMA 446 trend a predetermined distance from the first axis 428A, the user may interpret the PMA 446 as an indication that the instrument supplying the PMA data needs to be maintained and/or calibrated.

In some embodiments, the grid 416 or data display 212 (FIG. 2) may provide an indication in response to one or more portions of the PMA 446 exceeding a predetermined value or exceeding a predetermined value for a predetermined period of time. For example, the PMA 446 shown in FIG. 4 has drifted above the first axis 428A for a period. In response, the row 420K and/or the row 420L may be displayed in a different style (e.g., a different color) than the remaining rows. In some embodiments, a row with the PMA 446 either below the second axis 428B or above the third axis 428C may be displayed in a different style.

Figure 5:
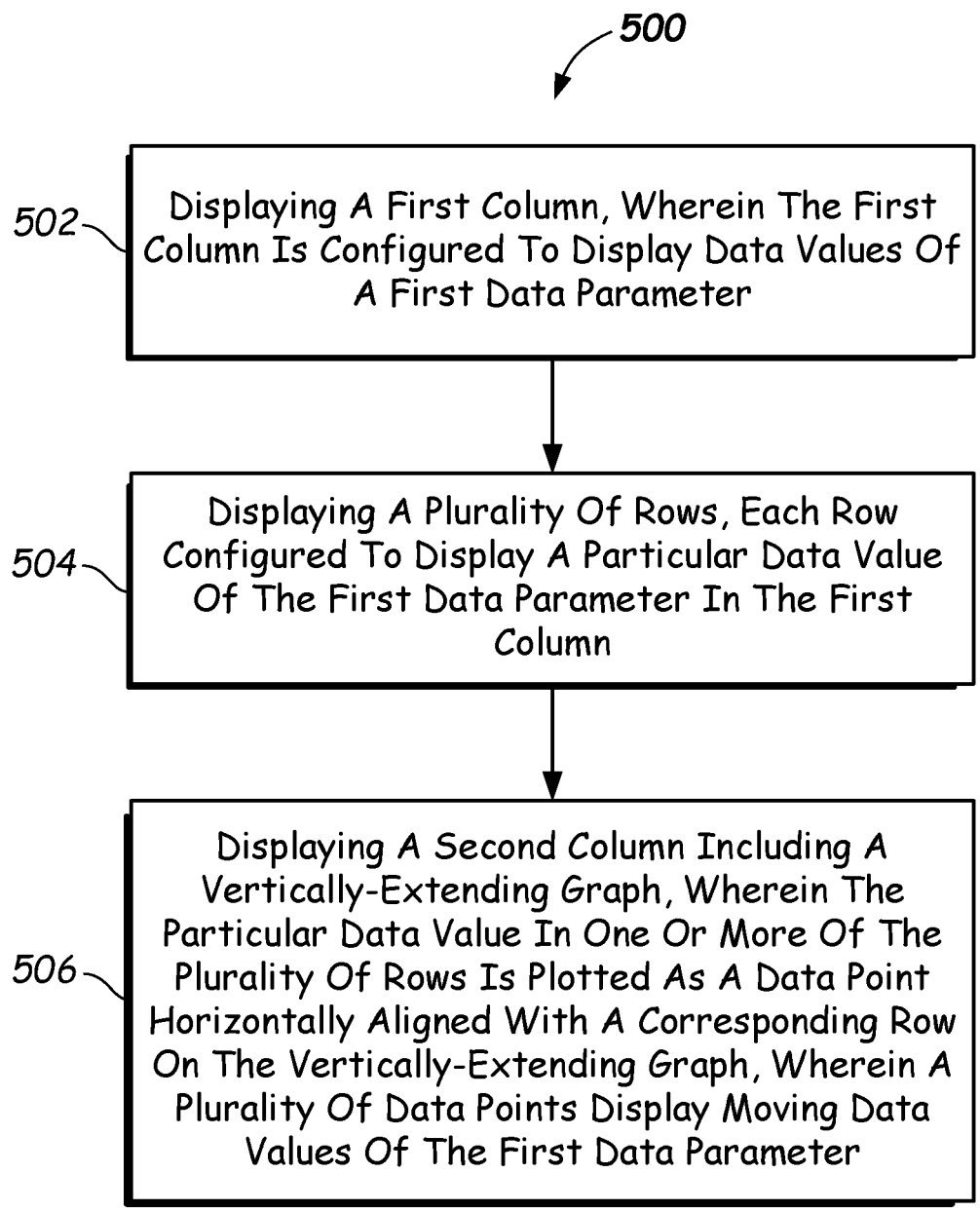
FIG. 5 illustrates a flowchart describing a method of displaying data according to one or more embodiments.

In another aspect, a method 500 of displaying data is disclosed and described in the flowchart of FIG. 5. The method 500 may include, in 502, displaying a first column (e.g., fourth column 318D), wherein the first column is configured to display particular data values of a first data parameter (e.g., quality control data or PMA, for example). The method 500 may include, in 504, displaying a plurality of rows (e.g., rows 320), each row configured to display a particular data value of the first data parameter in the first column. The method 500 may include, in 506, displaying a second column (e.g., fifth column 318E) including a vertically-extending graph (e.g., vertically-extending graph 326), wherein the particular data value in one or more of the plurality of rows is plotted as a data point (e.g., data points 327) horizontally aligned with a corresponding row on the vertically-extending graph, wherein a plurality of data points display moving data values of the first data parameter. Thus, the display illustrates both the raw data and a running plot of the data, all on one display image.

While the disclosure is susceptible to various modifications and alternative forms, specific embodiments and methods thereof have been shown by way of example in the drawings and are described in detail herein. It should be understood, however, that it is not intended to limit the invention to the particular systems or methods disclosed, but, to the contrary, the intention is to cover all modifications, equivalents and alternatives falling within the scope of the claims.

What is claimed is:

1. A data display coupled to a processor or server to cause the data display to display:
    a grid including:
        a first column configured to display data values of a first data parameter, each of the data values is a test result determined by and received from a same specimen analysis instrument coupled to the processor or server,
        a plurality of rows, each row configured to display only a particular one of the data values of the first data parameter in the first column, and
        a second column including a vertically-extending graph, wherein:
            the particular data value in one or more of the plurality of rows is plotted as a data point horizontally aligned with a corresponding row on the vertically-extending graph;
            a plurality of data points displays moving data values of the first data parameter;
            the vertically-extending graph comprises a vertically-extending line that represents moving average data values of the first data parameter;
            one or more moving average data values are calculated from five particular data values; and
            the five particular data values include a first particular data value in a first row, two particular data values in two rows prior to the first row, and two particular data values in two rows after the first row, wherein a moving average data value is calculated from the five particular data values and is plotted on the vertically-extending graph in horizontal alignment with the first row.

2. The data display of claim 1, wherein the first data parameter includes quality control values of an instrument.

3. The data display of claim 1, wherein the vertically-extending graph comprises:
    a first vertical axis; and
    a second vertical axis spaced from the first vertical axis and extending parallel to the first vertical axis,
    wherein a space between the first vertical axis and the second vertical axis represents a predetermined range of data values.

4. The data display of claim 3, wherein the data display is configured to generate an indication in response to one or more particular data values being outside of the predetermined range of data values.

5. The data display of claim 3, wherein the vertically-extending graph comprises a third vertical axis located between the first vertical axis and the second vertical axis, the third vertical axis representing a fixed data value.

6. The data display of claim 1, wherein the vertically-extending graph comprises a best-fit line extending vertically, the best-fit line generated at least in part using a plurality of particular data values.

7. The data display of claim 6, wherein the data display is configured to generate an indication in response to one or more portions of the best-fit line exceeding a predetermined value.

8. The data display of claim 1, wherein one or more rows are configured to be displayed in a first style in response to one or more particular data values displayed in the one or more rows being within a predetermined range of data values, and wherein one or more rows are configured to be displayed in a second style in response to one or more of the particular data values displayed in the one or more rows being outside the predetermined range of data values.

9. The data display of claim 8, wherein the first style is a first color and the second style is a second color.

10. The data display of claim 8, wherein the first style is a first intensity and the second style is a second intensity.

11. The data display of claim 1, wherein the data display is configured to generate an indication in response to one or more moving average data values exceeding a predetermined value.

12. The data display of claim 1, wherein the data display is configured to generate an indication in response to one or more moving average data values exceeding a predetermined value for a predetermined period of time.

13. The data display of claim 1, wherein one or more moving average data values are calculated from seven or more particular data values.

14. The data display of claim 13, wherein the seven or more particular data values include a first particular data value in a first row, three or more particular data values in three or more rows prior to the first row, and three or more particular data values in three or more rows after the first row, wherein a moving average data value is calculated from the seven or more particular data values and is plotted on the vertically-extending graph in horizontal alignment with the first row.

15. The data display of claim 1, wherein the grid further includes a third column configured to display data values of a second data parameter.

16. The data display of claim 15, wherein the second data parameter includes status of samples used to generate particular data values of the first data parameter.

17. A method of displaying data, comprising:
displaying a first column, wherein the first column is configured to display particular data values of a first data parameter, each of the particular data values is a test result determined by and received from a same specimen analysis instrument coupled to a processor or server causing the displaying of the first column;
displaying a plurality of rows, each row configured to display only a particular one of the data values of the first data parameter in the first column; and
displaying a second column including a vertically-extending graph, wherein:
the particular data value in one or more of the plurality of rows is plotted as a data point horizontally aligned with a corresponding row on the vertically-extending graph;
a plurality of data points displays moving data values of the first data parameter;
the vertically-extending graph comprises a vertically-extending line that represents moving average data values of the first data parameter;
one or more moving average data values are calculated from five particular data values; and
the five particular data values include a first particular data value in a first row, two particular data values in two rows prior to the first row, and two particular data values in two rows after the first row, wherein a moving average data value is calculated from the five particular data values and is plotted on the vertically-extending graph in horizontal alignment with the first row.

18. An instrument analyzer, comprising:
a memory storing data and programmed instructions or executable code;
a processor or server coupled to the memory and operative to execute the programmed instructions or executable code; and
a data display coupled to the processor or server to cause the data display to display:
a grid including:
a first column configured to display data values of a first data parameter, each of the data values is a test result determined by and received from a same specimen analysis instrument, the instrument coupled to the processor or server,
a plurality of rows, each row configured to display only a particular one of the data values of the first data parameter in the first column, and
a second column including a vertically-extending graph, wherein:
the particular data value in one or more of the plurality of rows is plotted as a data point horizontally aligned with a corresponding row on the vertically-extending graph;
a plurality of data points displays moving data values of the first data parameter received from the instrument;
the vertically-extending graph comprises a vertically-extending line that represents moving average data values of the first data parameter;
one or more moving average data values are calculated from five particular data values; and
the five particular data values include a first particular data value in a first row, two particular data values in two rows prior to the first row, and two particular data values in two rows after the first row, wherein a moving average data value is calculated from the five particular data values and is plotted on the vertically-extending graph in horizontal alignment with the first row.

* * * * *